Figure 1:
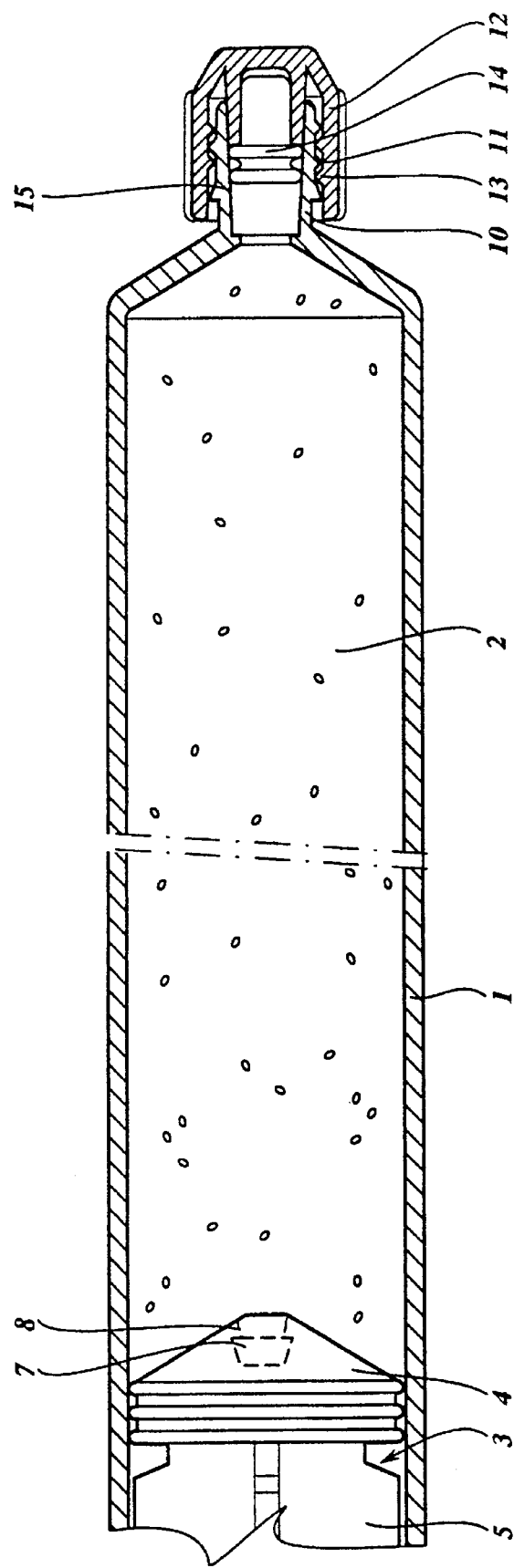

United States Patent [19]
van den Haak

[11] Patent Number: 5,584,817
[45] Date of Patent: Dec. 17, 1996

[54] PREFILLED INJECTION SYRINGE ASSEMBLY

[75] Inventor: Abraham van den Haak, Eesergroen, Netherlands

[73] Assignee: A.P.I.S. Medical B.V., TC Eesergroen, Netherlands

[21] Appl. No.: 288,110

[22] Filed: Aug. 10, 1994

[30] Foreign Application Priority Data

Jul. 15, 1994 [NL] Netherlands ............................ 9401173

[51] Int. Cl.⁶ .................................................. A61M 5/32
[52] U.S. Cl. ............................................. 604/195; 604/110
[58] Field of Search ..................................... 604/110, 192, 604/195, 196, 240, 242, 243

[56] References Cited

U.S. PATENT DOCUMENTS

| | | | |
|---|---|---|---|
| 4,281,653 | 8/1981 | Barta et al. | 604/192 |
| 5,221,262 | 6/1993 | Kite | 604/110 |
| 5,242,400 | 9/1993 | Blake, III | 604/110 |
| 5,290,233 | 3/1994 | Campbell | 604/110 |
| 5,330,440 | 7/1994 | Stanners et al. | 604/195 |

FOREIGN PATENT DOCUMENTS

| | | |
|---|---|---|
| 0360313 | 3/1990 | European Pat. Off. . |
| WO91/12842 | 9/1991 | WIPO . |

*Primary Examiner*—John D. Yasko
*Attorney, Agent, or Firm*—Kenyon & Kenyon

[57] ABSTRACT

An injection assembly, at least comprising a prefilled liquid container with an outflow opening, a piston displaceable in said liquid container with a piston rod and a piston head, an injection needle with a needle fitting which is or can be fixed in the outflow opening, and seling means, said needle fitting and the piston comprising coupling means which can be mutually coupled so as to allow the injection needle to be retracted into the liquid container after use of the assembly, the injection needle further comprising a protection cap with a passage for the needle, which cap is or can be permanently mounted on the outflow opening.

20 Claims, 10 Drawing Sheets

PREFILLED INJECTION SYRINGE ASSEMBLY

The present invention relates to an injection syringe assembly, comprising at least a prefilled liquid container with an outflow opening, a piston displaceable in said liquid container with a piston rod and a piston head, an injection needle with a needle fitting which is or can be fired in the outflow opening, and sealing means.

Such an injection syringe assembly is generally known. Prefilled injection syringe assemblies have a number of important advantages in comparison to more current injection syringes. Current injection syringes are generally filled by sucking liquid into the liquid container via the injection needle. Thereto the injection needle is inserted through a septum into a medicine vial or into the opening of a glass ampulla after breaking off the cap thereof. In both cases the extremity of the needle can be damaged, which will make the subsequent injection into the patient painful. Moreover, when sucking in from a medicine vial or the like, the needle can be contaminated at its outer side. Prefilled injection syringe assemblies are supplied with a liquid container filled under controlled conditions. Often a cap is mounted on the outflow opening, which is removed before use, after which an injection needle can be fixed.

These injection syringe assemblies are, in practice, reasonably satisfactory, but an important draw-back thereof is that, after use of the assembly for injecting a liquid into a patient, the needle is unprotected, and can easily lead to injuries. Moreover the assembly can be re-used. Injuries and re-use can lead to transfer of serious infectious diseases which may be incurable.

It is an object of the present invention to provide a solution for the above-mentioned draw-backs, and is, thereto, characterised in that the needle fitting and the piston comprise coupling means which can be mutually coupled so as to allow the injection needle to be retracted into the liquid container after use of the assembly, and in that the injection needle furthermore comprises a protection cap with a passage for the needle, which cap is or can be permanently mounted on the outflow opening.

Since the injection syringe assembly according to the invention offers the possibility to retract the injection needle after use into the liquid container, any risk of injuries by a used needle, as well as re-use, are avoided.

Since injection needles, in practice, are generally made of tubular material which is unwound from large coils, these needles are often slightly curved, so that, after retracting the needle into the container, it cannot be moved anymore through the opening in the protection cap.

In a preferred embodiment of the assembly according to the invention the coupling means of the needle fitting are made in the form of one or more lips with claws, and the coupling means of the piston are made in the form of a recess with an inwardly directed collar in the piston head, a positioning lug being present on one or more of the lips which can abut against a collar in the outflow opening, and can be released when coupling the piston with the needle fitting.

In this manner an injection syringe assembly is provided in which the piston head can be coupled with the needle fitting. Such an assembly can, in practice, be supplied provided with a cap.

Advantageously a portion of the needle fitting of the injection needle with the coupling means is situated in the outflow opening, and the sealing means are made in the form of a sealing element between the collar and the claws which, before use, can be pressed into the liquid container by means of the needle fitting.

In this case a special sealing on the needle is no longer required, and a sterile wrapping can be sufficient.

In another preferred embodiment of the injection syringe assembly according to the invention the needle fitting consists of two sections, that section of the needle fitting comprising the coupling means then being made in the form of an auxiliary coupling part which is situated in the outflow opening, and comprising, on the one hand, said coupling means, and, on the other hand, being adapted to be coupled with the other section of the needle fitting.

In this embodiment the injection syringe assembly is supplied with the auxiliary coupling part in the outflow opening, and, for reasons of sterility, a protection cap is fixed over the outflow opening. The advantage of this construction is that any desired injection needle suitable for the envisaged injection can be fixed by coupling the needle fitting and the auxiliary coupling part. The advantage thereof is that only one type of liquid container with an auxiliary coupling part is to be manufactured, and, depending on the envisaged injection, the injection needles can be additionally and separately supplied. By coupling the section of the needle fitting of the injection needle with the already mounted section of the needle fitting and the auxiliary coupling parts, and after fixing the protection cap, the sealing element is pressed into the liquid container, and the assembly is, then, ready for use.

Preferably the sealing element remains connected with the needle fitting during use. A consequence thereof is that the sealing element cannot become detached in the liquid container, and would, then, impede the movement of the piston, so that an optimal emptying of the liquid container is ensured.

In particular the dimensions of the sealing element are so that it can be accommodated in the recess in the piston. In this manner the so-called dead space in the liquid container is reduced to a minimum, and the latter can, then, be substantially completely emptied in use.

Particularly advantageously the protection cap comprises internal screw thread which cooperates with external screw thread on the outer side of the outflow opening. In this manner, and in the case that in the assembly as sold the sealing element is clamped between the claws and the inner collar, the assembly can be brought into operation in a simple manner. By (additionally) screwing the cap on the outflow opening, the sealing element and the claws can be moved past said collar, so that the injection syringe assembly is made ready for use.

Preferably a bevelled snap rib is present on the outer wall of the outflow opening, which can be permanently coupled with one or more snap lugs provided on the protection cap. The advantage thereof is that the assembly, after being used once, can no longer be opened, so that re-use is prevented.

In another special embodiment of the injection syringe assembly according to the invention, the piston comprises a piston rod and a piston head with a through-going filling duct therein and an element with septum operation near the piston head. In this embodiment the possibility is provided to fill the assembly through this filling duct.

In this embodiment, the element with septum operation is, preferably, movably arranged in the piston head in the recess near the open extremity thereof. When, prior to use, the element with septum operation is situated near the open end of the recess, this element will, after emptying the liquid container, be pressed further into the recess by the sealing element and the claws, so that the possibly remaining dead space in the liquid container will be reduced still further.

The injection syringe assembly can consist of materials currently used in prefilled syringes, often comprising glass and silicone rubber, although other materials which are inert in respect of the substances present in the liquid container may be used.

The invention provides, furthermore, an auxiliary coupling part intended for an injection syringe assembly according to the invention.

Finally an injection needle is provided, at least comprising a needle and a needle fitting, and intended for an injection syringe assembly according to the invention.

Figure 2:
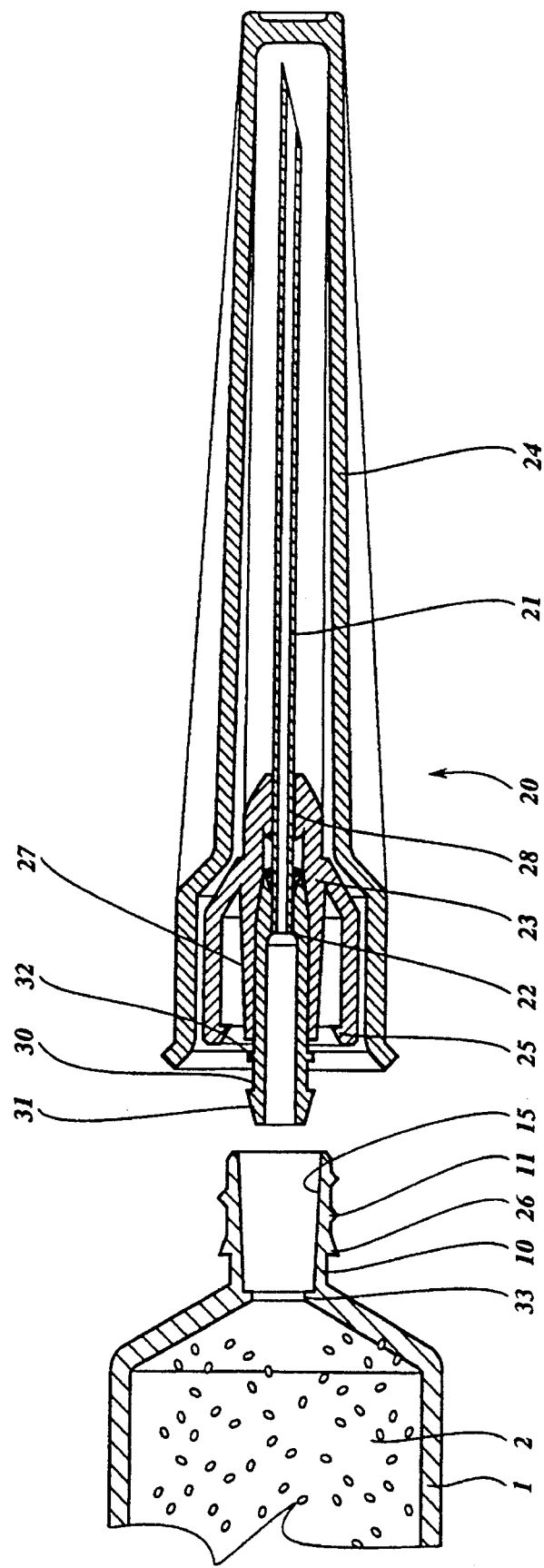
Figure 3:
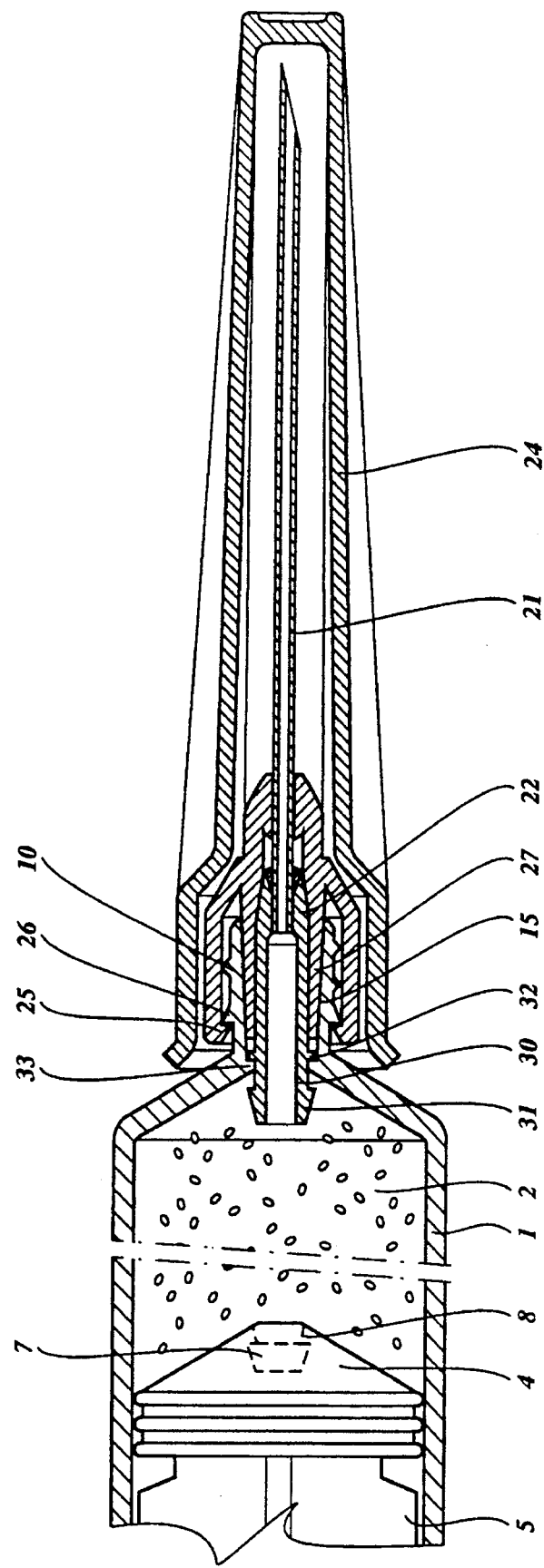
Figure 4:
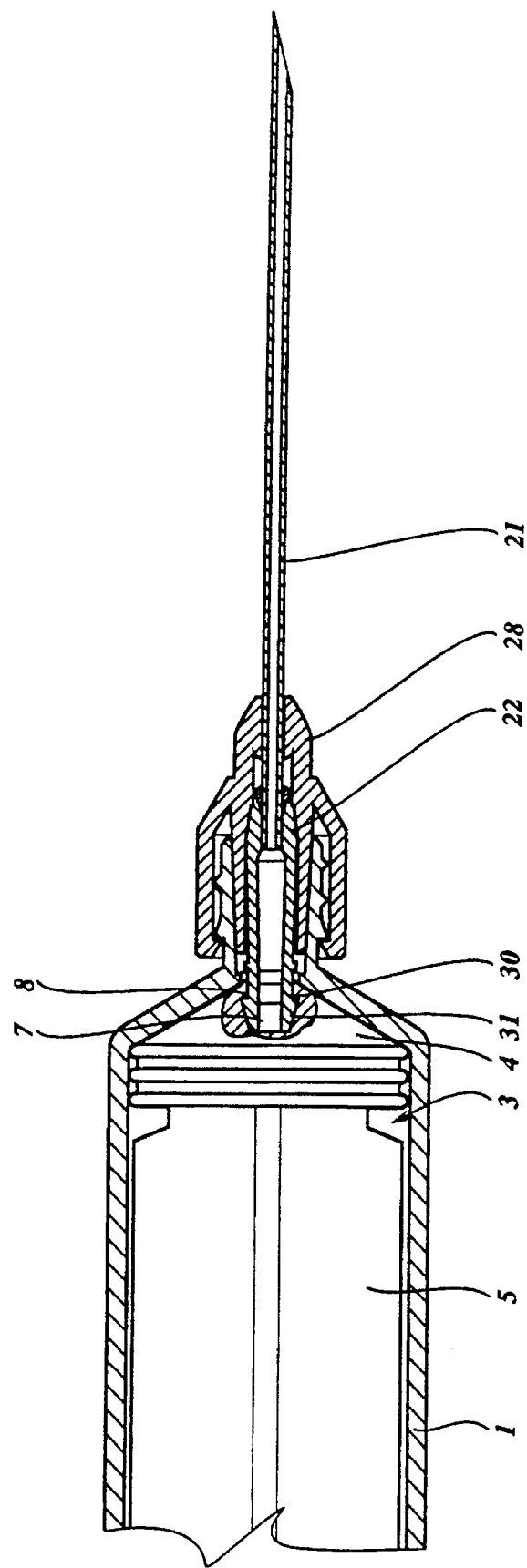
Figure 5:
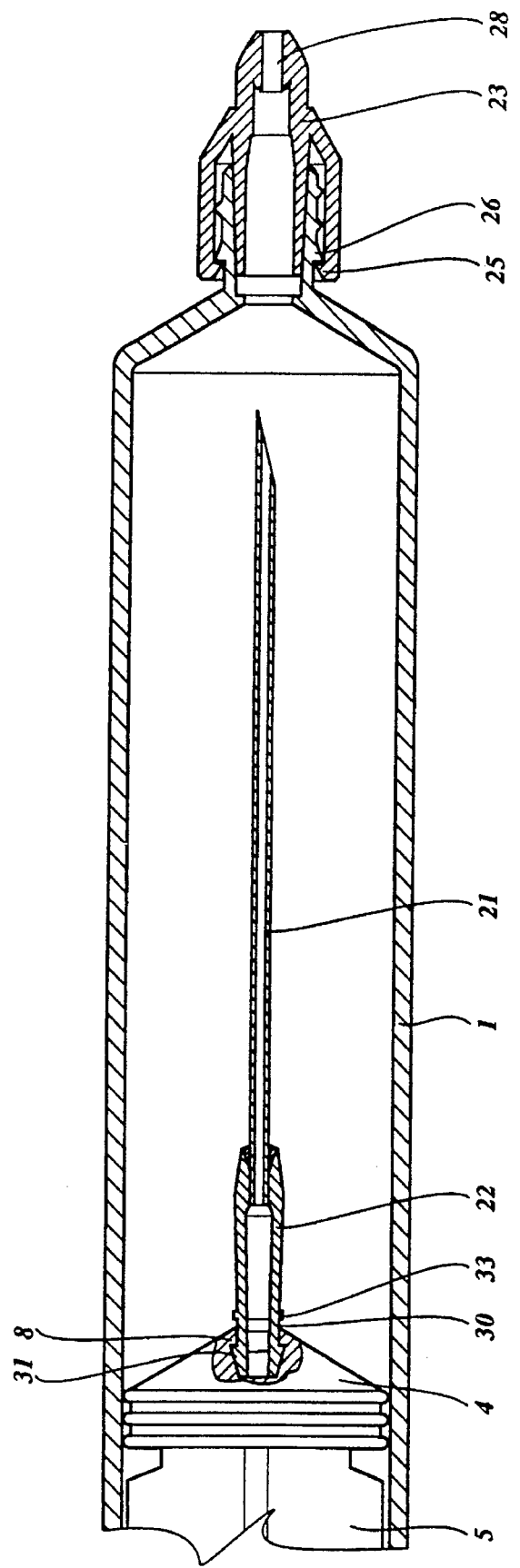
Figure 6:
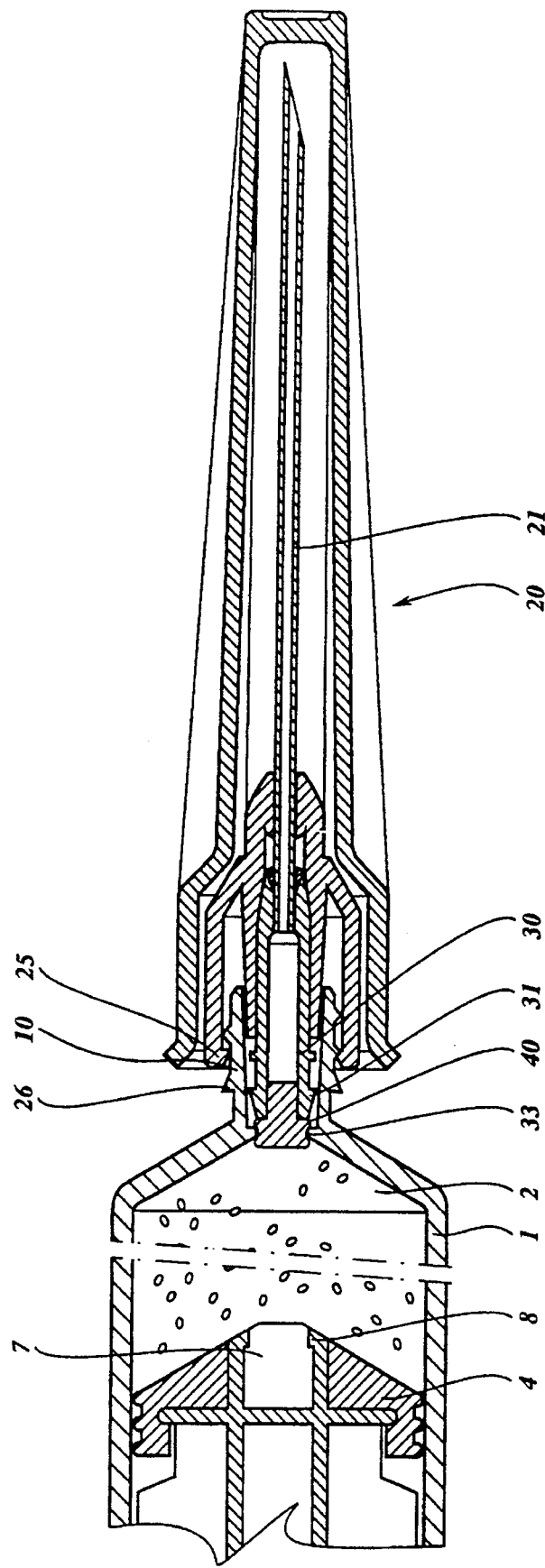
Figure 7:
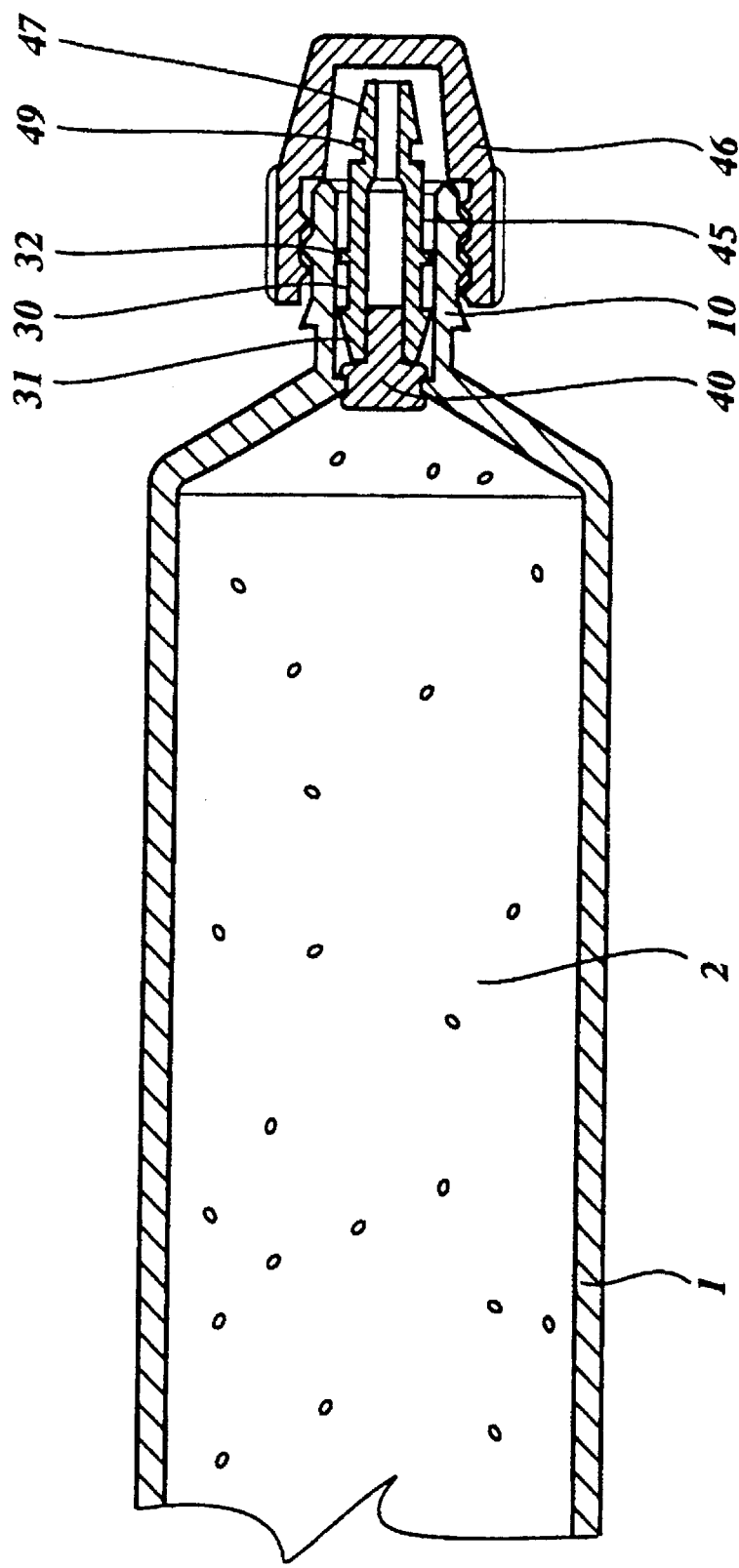
Figure 8:
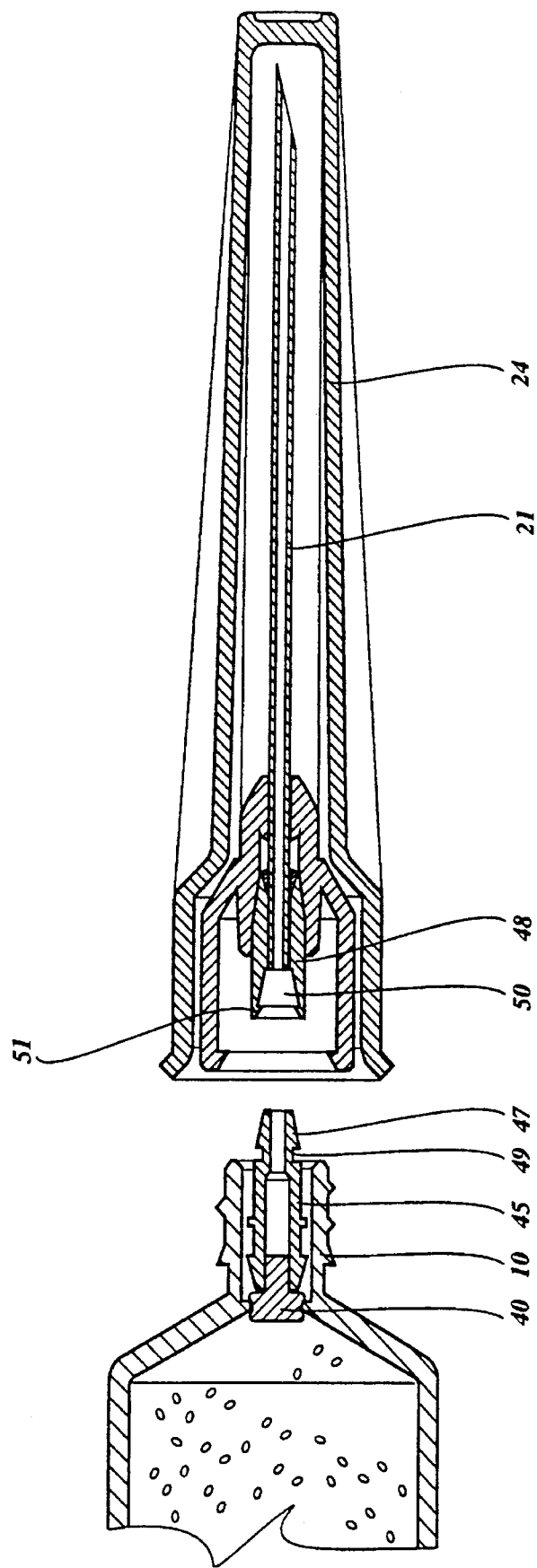
Figure 9:
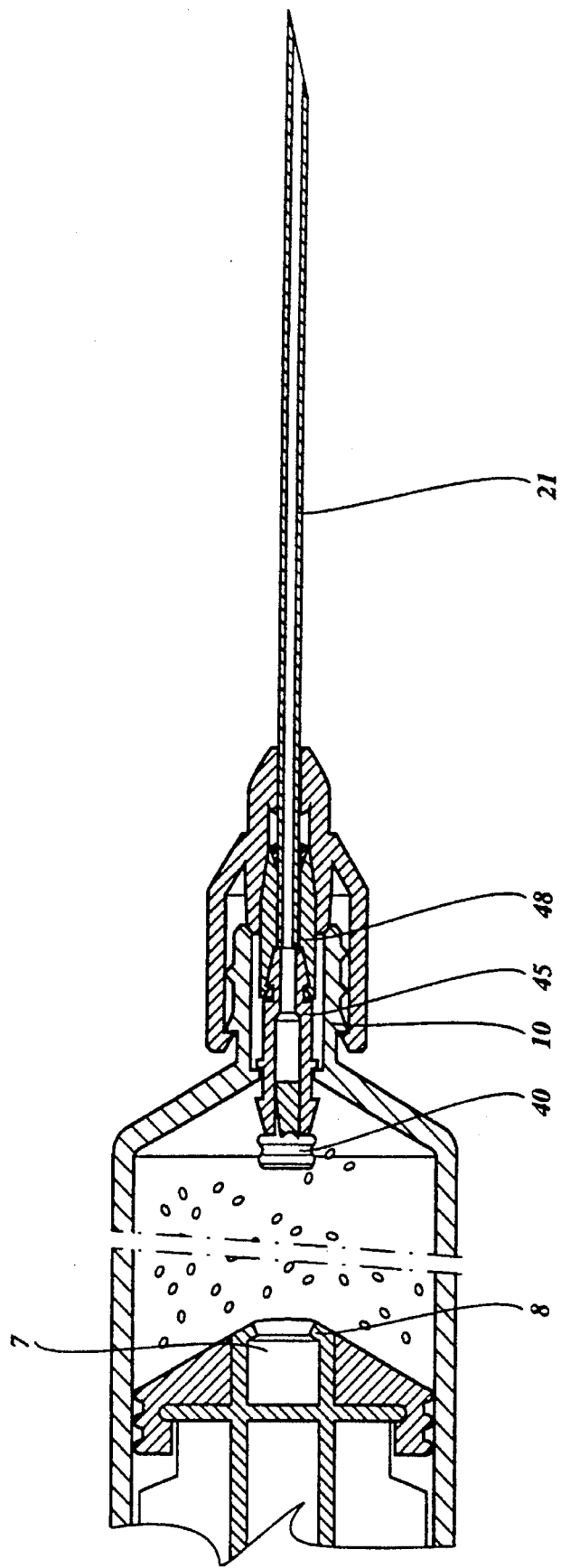
Figure 10:
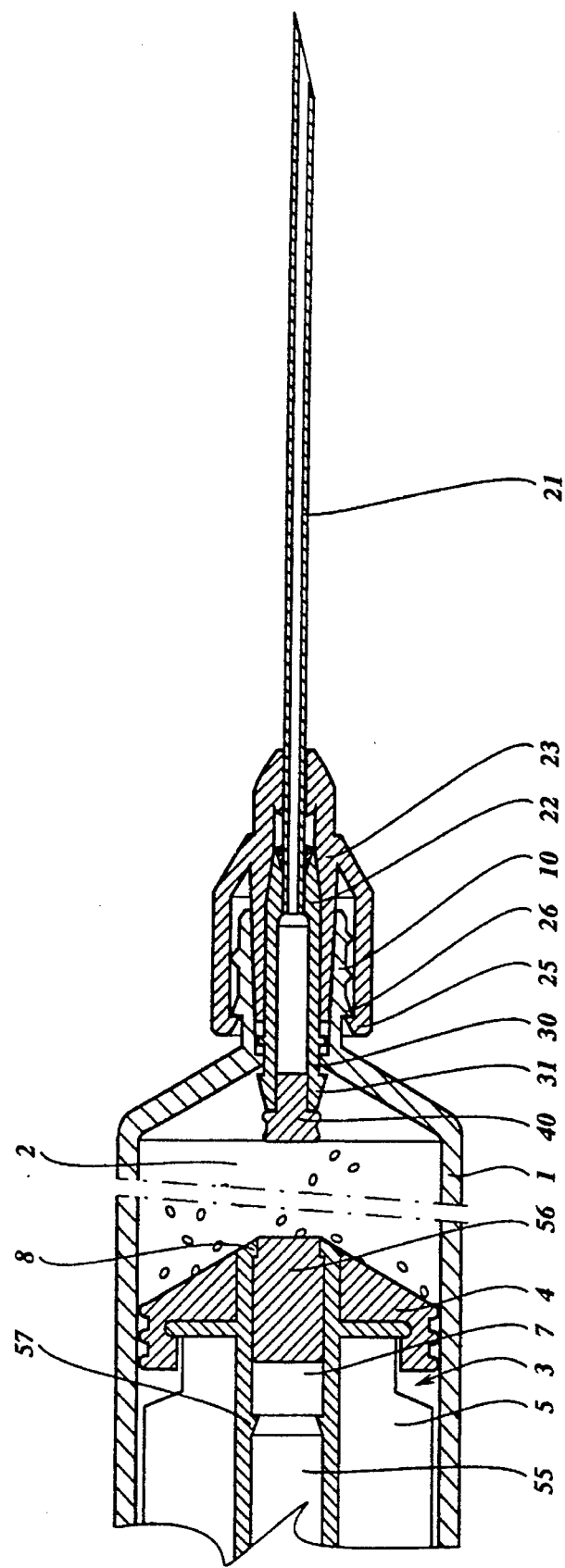

The invention will be elucidated below by reference to the appended drawing, showing in:

FIG. 1 a schematic cross-section of a prefilled injection syringe assembly according to the invention with a closing cap;

FIG. 2 the assembly of FIG. 1 with the cap being removed and an injection needle ready to be mounted;

FIG. 3 the assembly of FIG. 1 with a mounted injection needle;

FIG. 4 the assembly of FIG. 3 in the emptied condition, the needle fitting and the piston being coupled;

FIG. 5 the assembly of FIG. 4, the injection needle being retracted into the liquid container;

FIG. 6 another embodiment of an injection syringe assembly according to the invention with a mounted injection needle and a sealing element;

FIG. 7 still another embodiment of an injection syringe assembly according to the invention with an auxiliary coupling part with a sealing element and a closing cap;

FIG. 8 the embodiment of the assembly of FIG. 7 on which an associated injection needle can be fixed;

FIG. 9 the injection syringe assembly of FIG. 8 in the condition ready for use; and FIG. 10 a modification of the assembly of FIG. 6 with an element with septum operation in the piston head.

FIG. 1 shows a liquid container 1 with therein a liquid 2 to be injected. In said container 1 a piston 3 with a piston head 4 and a piston rod 5 can be shifted. In the piston head 4 a recess 7 with an inwardly directed collar 8 is provided.

The liquid container 1 comprises, moreover, an outflow opening 10 with external screw thread 11, on which a closing cap 12 with internal screw thread 13 is screwed. The closing cap 12 comprises a closing element 14 which seals against the inner wall 15 of the outflow opening 10. If required such a closing cap can be provided with a disruptable ring or tear strip or the like, which allows to indicate that it has been opened once.

In FIG. 2 the closing cap 12 has been removed, and an injection needle assembly 20 can be mounted. Said injection needle assembly comprises an injection needle 21 with a needle fitting 22 and a protection cap 23, these parts being surrounded by a needle sheath 24. Although not shown, generally also at the open extremity of the injection assembly 20 a closing cap or the like is provided, or the whole assembly is, as such, surrounded by a sterile wrapping.

As shown in FIG. 2, the injection needle assembly 20 can be fixed on the outflow opening in the direction of the arrow. During mounting snap lugs 25 provided on the protection cap will snap behind a circumferential collar 26 on the outflow opening. The portion 27 of the protection cap will then sealingly fit against the inner wall 15 of the outflow opening.

The needle fitting 22 is connected with the injection needle 21, but the protection cap 23 is a separate part with a through-going opening 28 through which the needle can be moved.

After mounting the injection needle assembly 20, the situation shown in FIG. 3 is reached, in which lips 30 with claws 31 project into the liquid container, lugs 32 provided on the lips 30 then lying against an inwardly directed collar 33 in the outflow opening 10. The needle fitting 22 is, at this moment, confined between the collar 33 and the cap 23, so that the injection needle is unambiguously mounted without the risk that the needle, during use, will be pressed into the liquid container.

Subsequently the sheath 24 is removed, and then the assembly is ready for use. As soon as the liquid 2 has been injected into a patient, the claws 31 will snap into the recess 7 in the piston head 4, and the lugs 32 of the collar 33 will be released as shown in FIG. 4, and by retracting the piston 3 the injection needle 21 with the needle fitting 22 can be retracted into the liquid container 1, the situation shown in FIG. 5 then being obtained.

In the condition of FIG. 5 it is not possible to move the injection needle 21 outwards again, since the needle 21 cannot be moved outwards through the opening 28. Needles are generally manufactured from tubular material which is supplied on large reels, so that the needles are always slightly curved. Moreover the passage 28 can be made in such a manner that it includes a slight angle with the longitudinal axis of the assembly.

Since the snap lugs 25 of the protection cap 23 rib behind the collar 26, the cap cannot be removed again, so that re-use of the needle is excluded. The assembly shown in FIG. 5 can be safely discarded without any risk of injuries or re-use.

The injection syringe assembly according to the invention requires from the user no complex or dangerous manipulations for protecting the needle, as is often the case with other assemblies.

When, in the preceding embodiment, the closing cap is removed, the assembly should be kept upright, since, otherwise, there is a risk that liquid drips out therefrom. In order to avoid this risk, the preferred embodiment of the injection syringe assembly according to the invention has already been provided with the injection needle assembly by the intermediary of a sealing element 40. All parts are, for the rest, the same as in the preceding Figs. The recess 7 in the piston head 4 has, in this case, such a dimension that the claws 31 with the sealing element 40 fit therein. The sealing element 40 is made of a preferably resilient sealing material such as silicone rubber or the like. As is clearly visible in FIG. 6, the injection needle assembly 20 is only partly fixed on the outflow opening 10, and the sealing element 40 is clamped between the claws 31 and the collar 33. By pressing the injection needle assembly 20 further onto the outflow opening, the lugs 25 snap behind the collar 26, the sealing element 40 then being pressed into the liquid container 1, whereafter the assembly is ready for use.

For the rest this assembly operates in the same way as the assembly according to the preceding Figs.

The sealing element 40 is clamped between the lips 30, and is, preferably, connected therewith, so as to prevent that it might freely land into the liquid container and would, then, impede the movement of the piston.

In FIG. 7 is a special embodiment of the injection syringe assembly according to the invention shown, in which the needle fitting 22 of the injection needle assembly 20 consists of two portions. The portion 45 is the so-called auxiliary coupling part, and is, prior to use, together with the sealing element 40, situated in the outflow opening 10, and is, for instance, covered by means of a closing cap 46. The auxiliary coupling part 45 comprises, as said before, lips 30 with the claws 31 and the lugs 32 on the one hand, and a chamfered extremity 47 with a circumferential recess 49 on the other hand, the latter serving for coupling with the other portion 48 of the needle fitting which is connected with the injection needle 21. Said portion 48 comprises a recess 50 with a snap rim 51 which can be sealingly coupled with the conical extremity 47 and the circumferential recess 49 of the auxiliary coupling part 45. This is shown in FIG. 8. After coupling of the portions 48 en 45 and removing the cap 23, the condition shown in FIG. 9 is obtained, and the assembly will then operate in the same manner as the embodiment of FIG. 6. Also in this embodiment there is no risk of liquid leaking from the outflow opening 10 during mounting.

In the embodiment shown in FIGS. 7 and 8, the conical extremity 47 extends from the outflow opening 10. The outflow opening can also be made so much longer that the portion 47 will situated completely in the outflow opening, and, after removing the cap 46, cannot be touched by the fingers of the user or be polluted in another way.

Finally FIG. 10 shows a special modified embodiment of the injection syringe assembly of FIG. 6, in which the piston has been constructed in a special way. The piston rod 5 and the piston head 4 comprise a through-going filling duct 55 in which an element with septum operation has been arranged. The recess 7 is, in this case, situated between the inwardly directed collar 8 and a second collar 57 in the filling duct 5. The advantage of this embodiment is that the liquid container 1 can be filled with a liquid 2 via the piston rod 5, i.e. the duct 55, by injecting this liquid by means of a filling needle through the element 56 into the liquid container.

The element 56 is advantageously fitted in the recess 7 in a shiftable manner, so that, at the end of the injection, the sealing element 40 with the claws 31 and the lips 30 can be shifted into said recess 7 by shifting the element 56. In this embodiment the dead space in the liquid holder is reduced to a minimum.

Moreover it is remarked that in all preceding embodiments of the injection syringe assembly according to the invention the protection cap 23 is not provided with screw thread but only with snap lugs 25 cooperating with the collar 26 on the outflow opening 10. It will be clear that this construction is user-friendly, since no rotational movement is required anymore as the injection needle assembly 20 can be snapped on the outflow opening 10. The use of internal screw thread is, of course, not excluded, and is even advantageous in the embodiment of FIG. 6, in which the needle fitting of the injection needle assembly 20 extends, as supplied, partly into the outflow opening, so as to allow the sealing element 40 to be clamped between the claws and the collar 33.

In the injection syringe assembly according to the invention, the injection needle is never in contact with the liquid to be injected during a long period, but only just before use of the assembly.

It will be clear that the injection syringe assembly is constructed in such a manner, that after use of the assembly the piston cannot be pulled out of the liquid container.

I claim:

1. An injection syringe assembly, comprising at least a prefilled liquid container with an outflow opening, a piston displaceable in said liquid container with a piston rod and a piston head, an injection needle with a needle fitting which is or can be fixed in the outflow opening, and sealing means, wherein the needle fitting and the piston comprise coupling means which can be mutually coupled so as to allow the injection needle to be retracted into the liquid container after use of the assembly, and wherein the injection needle further comprises a protection cap with a passage for the needle, which cap is or can be permanently mounted on the outflow opening wherein said coupling means of the needle fitting are made in the form of one or more lips with claws, and the coupling means of the piston are made in the form of a recess with an inwardly directed collar in the piston head, a positioning lug being present on one or more of the lips which can abut against a collar in the outflow opening and can be released when coupling the piston with the needle fitting.

2. The injection syringe assembly of claim 1, wherein a portion of the needle fitting of the injection needle with the coupling means is situated in the outflow opening, and the sealing means are made in the form of a sealing element between the collar and the claws which, before use, can be pressed into the liquid container by means of the needle fitting.

3. The injection syringe assembly of claim 1, wherein the needle fitting consists of two sections, the section of the needle fitting comprising the coupling means being made in the form of an auxiliary coupling part which is situated in the outflow opening and comprising said coupling means and being adapted to be coupled with the other section of the needle fitting.

4. The injection syringe assembly of claim 1, wherein the sealing element remains connected with the claws.

5. The injection syringe assembly of claim 4, wherein the dimensions of the sealing element are so that it can be accommodated in the recess in the piston.

6. The injection syringe assembly of claim 1, wherein the protection cap comprises internal screw thread which cooperates with external screw thread on the outer side of the outflow opening.

7. The injection syringe assembly of claim 1, wherein a bevelled snap rib is present on the outer wall of the outflow opening, which can be permanently coupled with one or more snap lugs provided on the protection cap.

8. The injection syringe assembly of claim 1, wherein the piston comprises a piston rod and a piston head with a through-going filling duct therein and an element with septum operation near the extremity of the piston head.

9. The injection syringe assembly of claim 8, wherein the element with septum operation is movably arranged in the piston head in the recess near the open extremity thereof.

10. An auxiliary coupling part intended for an injection syringe assembly according to claim 3.

11. An injection needle, at least comprising a needle and a needle fitting, and intended for an injection syringe assembly according to claim 1.

12. The injection syringe assembly of claim 2, wherein the needle fitting consists of two sections, the section of the needle fitting comprising the coupling means being made in the form of an auxiliary coupling part which is situated in the outflow opening and comprising said coupling means and being adapted to be coupled with the other section of the needle fitting.

13. The injection syringe assembly of claim 2, wherein the sealing element remains connected with the claws.

14. The injection syringe assembly of claim 3, wherein the sealing element remains connected with the claws.

15. The injection syringe assembly of claim 12, wherein the sealing element remains connected with the claws.

16. The injection syringe assembly of claim 13, wherein the dimensions of the sealing element are so that it can be accommodated in the recess in the piston.

17. The injection syringe assembly of claim 14, wherein the dimensions of the sealing element are so that it can be accommodated in the recess in the piston.

18. The injection syringe assembly of claim 15, wherein the dimensions of the sealing element are so that it can be accommodated in the recess in the piston.

19. The injection syringe assembly of claim 2, wherein the protection cap comprises internal screw thread which cooperates with external screw thread on the outer side of the outflow opening.

20. The injection syringe assembly of claim 3, wherein the protection cap comprises internal screw thread which cooperates with external screw thread on the outer side of the outflow opening.

* * * * *